United States Patent
Fazzio et al.

(10) Patent No.: US 7,512,415 B2
(45) Date of Patent: Mar. 31, 2009

(54) METHOD AND SYSTEM FOR PRODUCING A SCENT FROM A HAND-HELD DEVICE

(75) Inventors: Ronald Shane Fazzio, Loveland, CO (US); Richard C Ruby, Menlo Park, CA (US)

(73) Assignee: Avago Technologies General IP (Singapore) Pte. Ltd., Singapore (SG)

( * ) Notice: Subject to any disclaimer, the term of this patent is extended or adjusted under 35 U.S.C. 154(b) by 738 days.

(21) Appl. No.: 11/144,559

(22) Filed: Jun. 3, 2005

(65) Prior Publication Data

US 2006/0293871 A1 Dec. 28, 2006

(51) Int. Cl.
*H04M 1/00* (2006.01)

(52) U.S. Cl. ............... 455/556.1; 455/557; 455/558; 455/567; 455/550.1; 455/575.1; 455/90.1; 222/145.1; 222/145.5; 222/145.6; 222/52; 222/94

(58) Field of Classification Search ............ 455/550.1, 455/556.1–2, 557–558, 567, 575.1, 90.1–2; 222/145.1, 145.5, 145.6, 52, 94, 136; 239/302–315
See application file for complete search history.

(56) References Cited

U.S. PATENT DOCUMENTS

| | | | |
|---|---|---|---|
| 5,969,353 A | 10/1999 | Hsieh | |
| 6,323,912 B1 | 11/2001 | McIntyre | |
| 6,378,988 B1 | 4/2002 | Taylor et al. | |
| 6,390,453 B1 | 5/2002 | Frederickson et al. | |
| 6,554,203 B2 * | 4/2003 | Hess et al. | 239/69 |
| 7,073,731 B2 * | 7/2006 | Hess et al. | 239/306 |
| 7,152,758 B2 * | 12/2006 | Fazzio et al. | 222/145.1 |
| 2002/0176802 A1 | 11/2002 | Chung et al. | |
| 2003/0116195 A1 | 6/2003 | Weissgerber et al. | |
| 2004/0203412 A1 | 10/2004 | Greco et al. | |
| 2004/0204043 A1 | 10/2004 | Wang et al. | |
| 2004/0235430 A1 | 11/2004 | Ma et al. | |

* cited by examiner

*Primary Examiner*—Tuan A Tran (57) ABSTRACT

A technique for producing a scent from a hand-held device involves receiving a scent mixture formula at a hand-held device, converting the scent mixture formula into dispense control signals, and generating a scent mixture in response to the dispense control signals, the scent mixture being generated from different base scents that are individually stored within the hand-held device. In an embodiment, the scent mixture formula includes a scent identifier and a scent quantifier related to each base scent that is used to generate the scent mixture. Mixing multiple base scents to generate scent mixtures greatly expands the range of different scents that can be generated at a hand-held device that stores a limited number of base scents. Further, encoding a scent mixture into a scent mixture formula enables scent mixtures to be easily shared between hand-held devices.

19 Claims, 7 Drawing Sheets

| availability 148 | scent ID 106 | scent quantifier 108 |
| availability 148 | scent ID 106 | scent quantifier 108 |
| availability 148 | scent ID 106 | scent quantifier 108 |
| availability 148 | scent ID 106 | scent quantifier 108 |
| availability 148 | scent ID 106 | scent quantifier 108 |
| dispense characteristics 150 |||
| other 152 |||

METHOD AND SYSTEM FOR PRODUCING A SCENT FROM A HAND-HELD DEVICE

BACKGROUND OF THE INVENTION

There are many different types of electronic hand-held devices including mobile phones, personal digital assistants (PDAs), and music players (e.g., MP3 players). These hand-held devices appeal to a user's sense of sight through graphical user interfaces and to the user's sense of sound through speakers and microphones. Although sight and sound are effective in producing an acceptable user experience, the user experience provided by hand-held devices may be enhanced if the hand-held devices were able to appeal to other senses.

Some hand-held devices have been configured to store and dispense a scented material as a way of enhancing the user experience. Further, some hand-held devices have been configured to store multiple different scented materials. The different scented materials can be dispensed one at a time to release the corresponding scent. One drawback to these hand-held devices is that the number of scents that can be dispensed from the hand-held devices is the same as the number of different scented materials stored in the device.

SUMMARY OF THE INVENTION

A technique for producing a scent from a hand-held device involves receiving a scent mixture formula at a hand-held device, converting the scent mixture formula into dispense control signals, and generating a scent mixture in response to the dispense control signals, the scent mixture being generated from different base scents that are individually stored within the hand-held device. In an embodiment, the scent mixture formula includes a scent identifier and a scent quantifier related to each base scent that is used to generate the scent mixture. Mixing multiple base scents to generate scent mixtures greatly expands the range of different scents that can be generated at a hand-held device that stores a limited number of base scents. Further, encoding a scent mixture into a scent mixture formula enables scent mixtures to be easily shared between hand-held devices.

The scent mixture formula may also include information related to dispense characteristics of the scent mixture. For example, dispense characteristics may include the time of dispense, the duration of dispense, the quantity of dispense, whether or not the dispensing is to be repeated, the interval of dispensing, etc. Incorporating dispense characteristics into the scent mixture formula further enhances the ability to customize the generation of scents at a hand-held device and enhances the user experience.

Other aspects and advantages of the present invention will become apparent from the following detailed description, taken in conjunction with the accompanying drawings, illustrated by way of example of the principles of the invention.

BRIEF DESCRIPTION OF THE DRAWINGS

Throughout the description similar reference numbers are used to identify similar elements.

DETAILED DESCRIPTION

A technique for producing a scent from a hand-held device involves receiving a scent mixture formula at a hand-held device, converting the scent mixture formula into dispense control signals, and generating a scent mixture in response to the dispense control signals, the scent mixture being generated from different base scents that are individually stored within the hand-held device. In an embodiment, the scent mixture formula includes a scent identifier and a scent quantifier related to each base scent that is used to generate the scent mixture.

Figure 1:
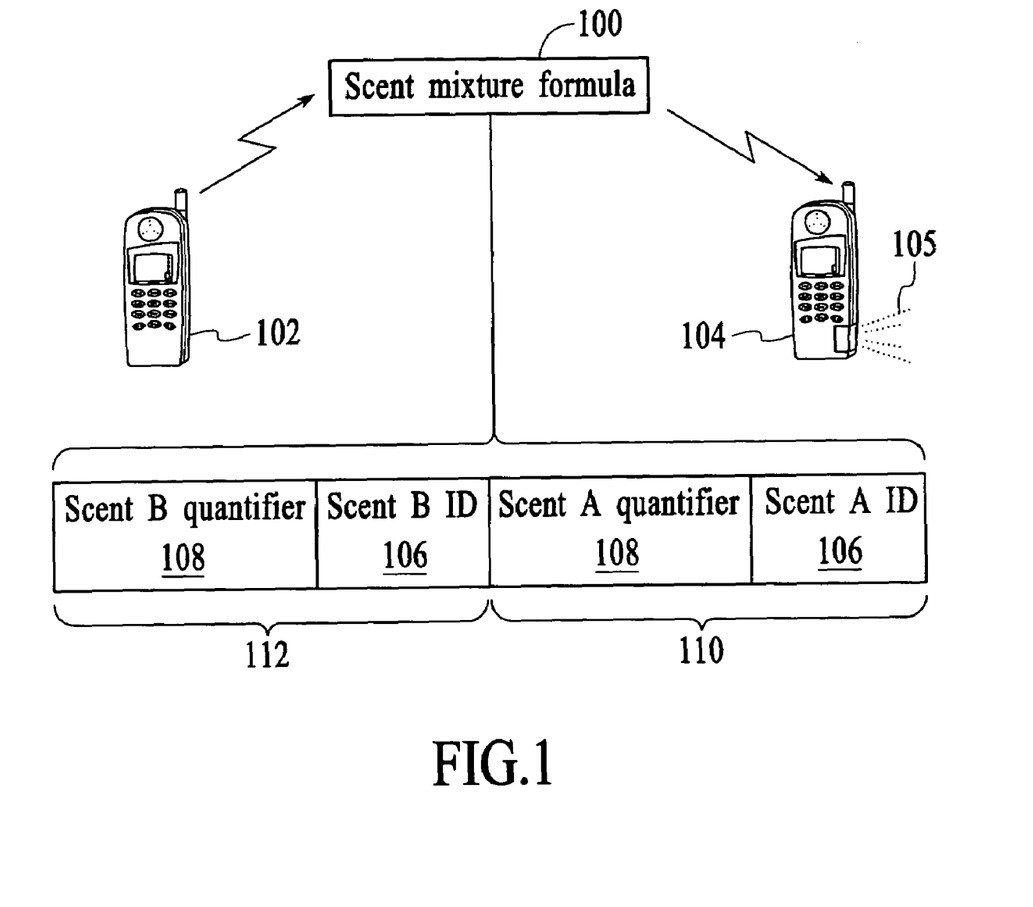
FIG. 1 illustrates the wireless transmission of a scent mixture formula from one hand-held device to another hand-held device.

FIG. 1 illustrates the wireless transmission of a scent mixture formula 100 from one hand-held device 102 to another hand-held device 104. A scent mixture formula indicates components of a scent mixture 105 that consists of two or more base scents. In an embodiment of the invention, a scent mixture formula includes a scent identifier (ID) 106 and a scent quantifier 108 related to each base scent that is used to generate the scent mixture. The scent ID indicates a particular base scent and may include, for example, a scent name, a scent ID number, or any other digital encoding of a scent identifier. In an embodiment, base scents are identified by scent names, with the scent names being translated into digital values. The scent quantifier is a quantifiable property, including, for example, a percentage, a proportion, an absolute amount, or any other quantifiable property that can be expressed as a digital value. In an embodiment, the scent quantifier identifies a percentage or proportion of the base scent identified by the corresponding scent ID in the total composition of a scent mixture. For example, the scent quantifier indicates what percentage of the total scent mixture should come from the base scent identified by the corresponding scent ID. In another embodiment, the scent quantifier indicates a specific amount of a base scent that is to be dispensed to generate a scent mixture. As indicated by the expanded view of the scent mixture formula in FIG. 1, the scent mixture formula includes a scent ID and scent quantifier pair 110 for base scent A and a scent ID and scent quantifier pair 112 for base scent B. Although the scent mixture formula depicted in FIG. 1 includes only two base scents, scent mixture formulas that include more than two base scents are possible. Additionally, the configuration of the scent mixture formula encoding (e.g., scent ID before scent quantifier or scent quantifier before scent ID, etc.) can be different from that shown in FIG. 1.

The scent mixture formula is used by the receiving hand-held device to generate the specified scent mixture. The use of a scent mixture formula to generate a scent mixture from multiple different base scents is described in more detail below.

Figure 2:
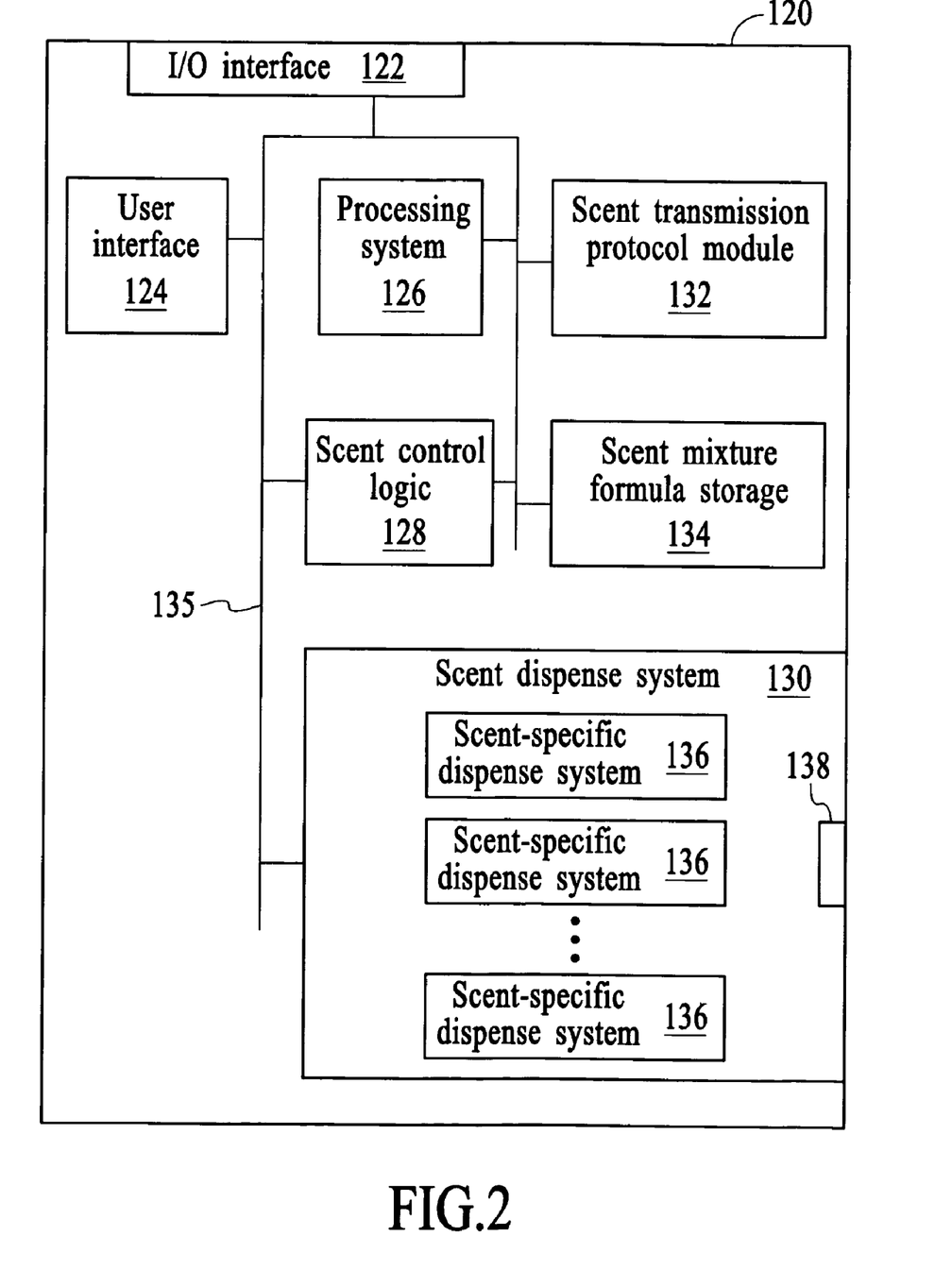
FIG. 2 depicts an embodiment of a hand-held device that can be used to transmit a scent mixture formula to another device or to generate a scent mixture upon receiving a scent mixture formula.

FIG. 2 depicts an embodiment of a hand-held device 120 that can be used to transmit a scent mixture formula to another device or to generate a scent mixture upon receiving a scent mixture formula as depicted in FIG. 1. Examples of devices that may be used to transmit a scent mixture formula to another hand-held device or to generate a scent mixture upon receiving a scent mixture formula include mobile phones, PDAs, music players, and other types of hand-held devices. The hand-held device of FIG. 2 includes an input/output (I/O) interface 122, a user interface 124, a processing system 126, scent control logic 128, and a scent dispense system 130. The hand-held device may also include a scent transmission protocol module 132 and scent mixture formula storage 134. The various elements of the hand-held device are connected by a signal path 135, although other configurations or techniques for communicating between elements are possible. The elements of the hand-held device are described below followed by descriptions of transmitting a scent mixture formula using the hand-held device, processing a received scent mixture formula using the hand-held device, and generating a scent mixture from a scent mixture formula using the hand-held device. The hand-held device 120 described with reference to FIG. 2 can be used as the hand-held devices 102 and 104 from FIG. 1.

Referring to FIG. 2, the user interface 124 of the hand-held device 120 allows a user to control the hand-held device and may include any type of user interface, for example, a display screen, a keypad, a touch screen, a pen-based system, a voice activated system, or any combination thereof. The user interface can be used to control the transmission of a scent mixture formula, the reception of a scent mixture formula, the storage of scent-mixture formulas, and the generation of a scent mixture. User interfaces for hand-held devices are well-known and the type of user interface is not critical to the invention.

The I/O interface 122 of the hand-held device 120 supports communications with other devices or systems. For example, the I/O interface is a wireless interface such as those used in mobile phones and PDAs. Wireless interfaces are well-known in the field of hand-held devices. The I/O interface may alternatively be any other type of I/O interface such as an infrared or wireline interface. The hand-held device may include multiple different I/O interfaces.

The processing system 126 of the hand-held device 120 performs the processing to support operation of the hand-held device. The processing system may include hardware, software, firmware or any combination thereof. For example, in a mobile phone or a PDA, the processing system may include memory and a processor for storing and executing computer code. The processor may be a general function processor, an application specific integrated circuit (ASIC), or any combination thereof. Alternatively, the processor may be as simple as an analog circuit. The memory may be ROM, RAM, Flash, a hard disk, or any combination thereof. The memory may also be a removable storage media, for example, a USB drive, Memory Stick, compact flash, Secure Digital, external hard-drive, CD, CD-R, CD-RW, DVD, DVD±R, DVD-ROM, DVD±RW, Zip drive, Jazz drive, or any other type of removable storage or any combination thereof.

The scent mixture formula storage 134 depicted in FIG. 2 is memory that stores one or more scent mixture formulas. The scent mixture formula storage may be dedicated memory or general purpose memory including, for example, ROM, RAM, Flash, a hard disk, or any combination thereof. Storage module 134 may be a fixed storage media or removable storage media. Examples of removable storage media include a USB drive, Memory Stick, compact flash, Secure Digital, external hard-drive, CD, CD-R, CD-RW, DVD, DVD±R, DVD-ROM, DVD±RW, Zip drive, Jazz drive, or any other type of removable storage media or any combination thereof. In the embodiment of FIG. 2, the scent mixture formula is general purpose Flash memory that is integrated into the hand-held device.

The scent transmission protocol module 132 manages the communication of scent related information between the hand-held device and another device according to a scent transmission protocol. In an embodiment, the scent transmission protocol module includes computer code that is stored in memory such as ROM or Flash and executed by the processing system as needed. The scent transmission protocol module may alternatively be embodied as an ASIC. A further description of the scent transmission protocol is provided below. In an embodiment, the scent transmission protocol may be implemented by the processing system, an ASIC, or a combination thereof.

The scent control logic 128 of the hand-held device 120 supports operation of the scent dispense system 130. In particular, the scent control logic converts a scent mixture formula into dispense control signals that are used to drive the scent dispense system. The scent control signals may be, for example, analog voltage or current signals or digital signals depending on the scent dispense system. The scent control logic may include hardware, software, firmware or any combination thereof. Although the scent control logic is shown as a separate functional element from the processing system 126 and the scent dispense system 130 for description purposes, the scent control logic may be partially or fully integrated within the processing system and/or the scent dispense system of the hand-held device.

The scent dispense system 130 of the hand-held device 120 functions to dispense scents from the hand-held device in response to dispense control signals. The scent dispense system can be configured to dispense a scent mixture from the hand-held device or to dispense individual base scents from the hand-held device that are mixed upon dispensing. The scent dispense system includes multiple scent-specific dispense systems 136 and a scent output 138. Each of the scent-specific dispense systems individually stores different base scents. The number of different base scents that can be stored within the hand-held device ranges from two to N, where N is an integer greater than two.

The scent-specific dispense systems 136 individually store different base scents that are internally or externally mixed to generate the scent mixture. Implementation details of the scent-specific dispense systems and the output 138 depend on the type of materials that are stored in the scent-specific dispense systems and the technique that is used to dispense the base scents from the scent-specific dispense systems. The base scents may be stored in the scent-specific dispense systems as fluids or solids under standard temperature and pressure conditions. The dispense systems may utilize, for example, piezoelectric, thermal, chemical release, photo release, electrical, electrochemical, mechanical, or pneumatic techniques or any combination thereof to dispense the base scents involved. The scent-specific dispense systems may dispense the base scents as, for example, a spray, a drop or drops, a liquid stream, a vapor, an aerosol, or a gas. In an embodiment, the scent-specific dispense systems include reservoirs, such as chambers formed in a substrate material, in which the base scents are stored. The reservoirs may be configured for single use or may be refillable. The scent dispense system 130, the scent-specific dispense systems, or any portion thereof may be removable from the hand-held device 120 for replacement or refilling of the base scents. Examples of removable scent dispense systems are described in the U.S. patent application entitled "A scented material dispense system for a hand-held device," Ser. No. 10/919,669, filed on Aug. 17, 2004, which is assigned to the assignee of the current invention and incorporated by reference herein.

In an embodiment, the different base scents are stored in a solid form in the scent dispense system 130. For example, the different base scents are stored as wax-like materials in which scented molecules are held together by a binding agent. Techniques for dispensing a base scent that is stored in a solid form may include heating the solid material to transform the solid material into a vapor that can be transported through the system and dispensed from the system. The scent dispense system may include a combination of channels, nozzles, and supporting mechanism(s) to move the vaporized base scents out of the scent dispense system.

In another embodiment, the base scents are stored in the scent dispense system 130 as fluids. The fluids can be dispensed using, for example, microfluidic techniques. Microfluidic techniques for dispensing scented fluids may include, for example, piezoelectric, thermal, chemical release, photo release, electrical, electrochemical, mechanical, or pneumatic techniques, or any combination thereof. Again, the scent dispense system may include a combination of channels, nozzles, and supporting microfluidic mechanisms to move the scented fluids out of the scent dispensing system.

In still another embodiment, the base scents are stored in the scent dispense system 130 in a microencapsulated form. The microencapsulated base scents may be, for example, released from microencapsulation upon dispensing or dispensed from the scent dispense system in a microencapsulated form and subsequently released, for example, by physical contact such as rubbing.

As indicated above, there are many different techniques that can be used to store and dispense the base scents. The particular technique used to store and dispense the base scents is not critical to the invention as long as the scent dispense system 130 enables at least two different base scents to be mixed either internally or upon being dispensed from the hand-held device 120. The base scents are mixed to form the scent mixture that is specified by the scent mixture formula.

Figure 3:
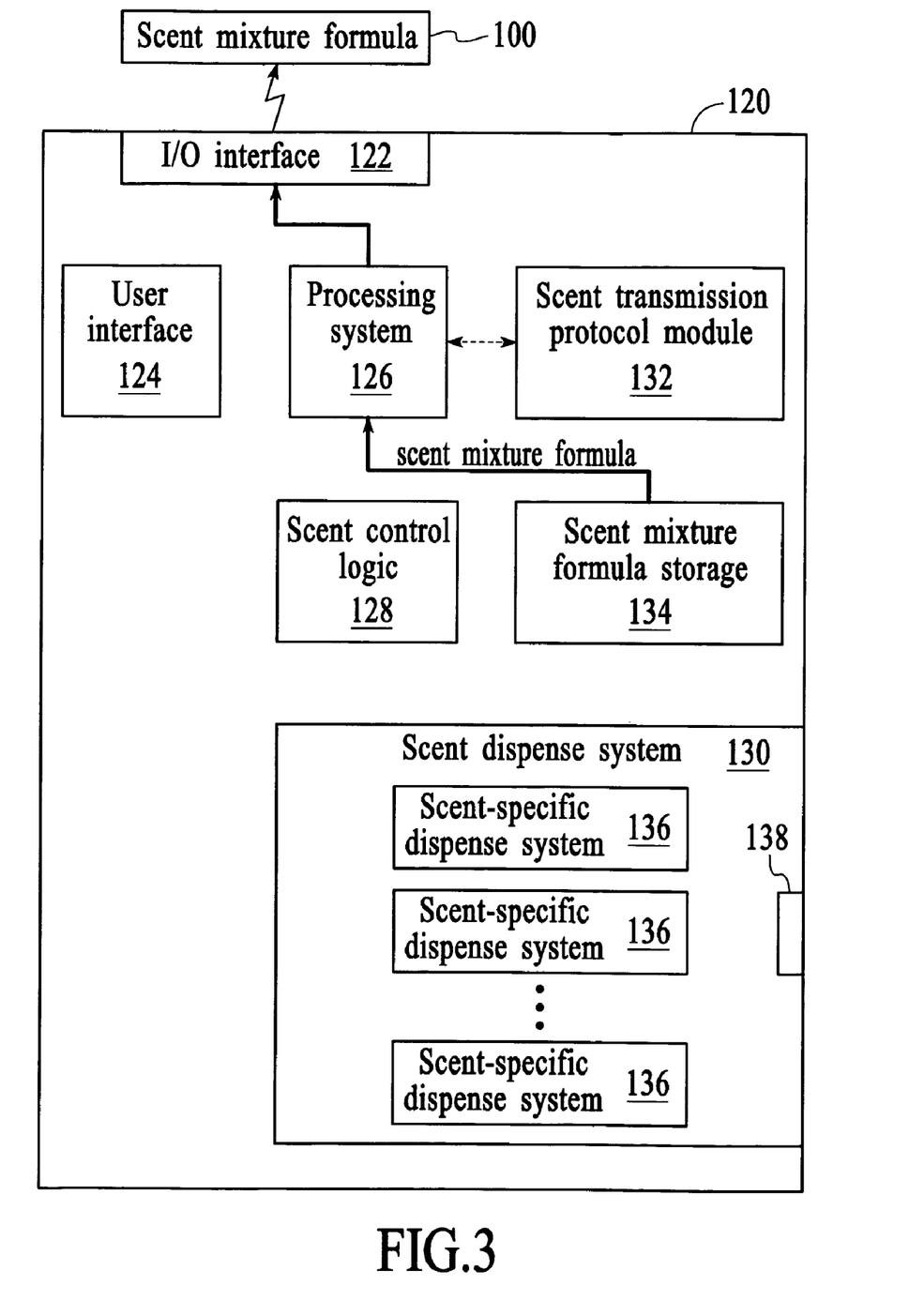
FIG. 3 illustrates the operation of transmitting a scent mixture formula from a hand-held device.

An exemplary operation of transmitting a scent mixture formula from a hand-held device is now described with reference to FIG. 3. In the example of FIG. 3, a scent mixture formula is stored in the scent mixture formula storage 134 of the hand-held device 120. The scent mixture formula can be obtained by the hand-held device in various different ways including, for example, by the scent mixture formula being entered into the hand-held device through the user interface 124, by receiving the scent mixture formula from another hand-held device, or by downloading the scent mixture formula from a database of scent mixture formulas.

Once the scent mixture formula is stored within the hand-held device 120, the stored scent mixture formula is obtained by the processing system 126. In the embodiment of FIG. 3, the processing system incorporates the scent mixture formula into a known communications protocol. The processing system may utilize the scent transmission protocol module 132 to encode the scent mixture formula. For example, the processing system may encapsulate the scent mixture formula into one or more internet protocol (IP) packets. The scent mixture formula is then provided to the I/O interface 122 for transmission. In the embodiment of FIG. 3, the I/O interface transmits the scent mixture formula 100 using a known wireless communications protocol. The scent mixture formula is transmitted, for example, to a hand-held device that is capable of generating the scent mixture, to a device that is capable of decoding the scent mixture formula but not generating the scent mixture, or to a device that is not capable of either decoding the scent mixture formula or generating the scent mixture.

Figure 4:
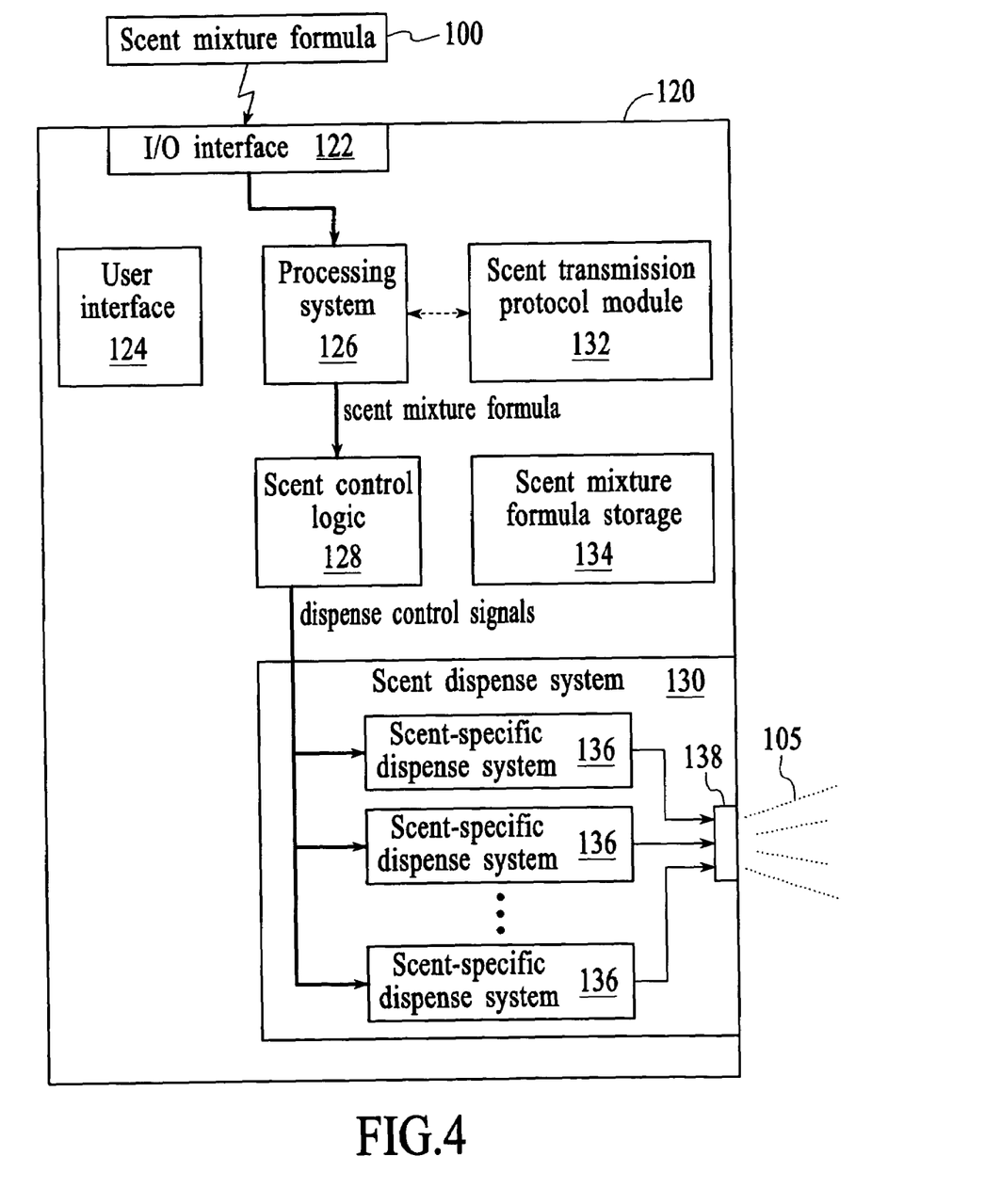
FIG. 4 illustrates the operation of receiving a scent mixture formula at a hand-held device and generating a scent mixture in response to the scent mixture formula.

An exemplary operation of receiving a scent mixture formula and generating a scent mixture in response to the scent mixture formula is described with reference to FIG. 4. In the example of FIG. 4, a transmission that includes a scent mixture formula 100 is received at the I/O interface 122 of the hand-held device 120. The I/O interface processes the received transmission and forwards the relevant data to the processing system 126. For example, the I/O interface strips off transmission overhead and forwards the non-overhead data (e.g., IP packets) to the processing system. The processing system receives the data from the I/O interface and recognizes at least a portion of the data as a scent mixture formula. Once recognized, the scent mixture formula is forwarded to the scent control logic 128. The processing system may utilize the scent transmission protocol module 132 to decode the scent mixture formula. The scent control logic converts the scent mixture formula into dispense control signals that are used to drive the appropriate scent-specific dispense systems 136 of the scent dispense system 130. The scent-specific dispense systems are driven in response to the dispense control signals to dispense the specified scented materials in the specified quantities to generate the scent mixture 105 that is identified by the scent mixture formula.

In an embodiment, the scent mixture formula includes information related to dispense characteristics for the scent mixture. Information related to scent characteristics may include, for example, the time of dispense, the duration of dispense, the quantity of dispense, whether or not the dispensing is to be repeated, the interval of dispensing, etc. Although some dispense characteristics are identified, other characteristics related to dispensing a scent mixture can be specified in the scent mixture formula.

The generation of the scent mixture specified by the received scent mixture formula can be triggered in different ways. In one embodiment, generation of the scent mixture specified by the received scent mixture formula is triggered by receiving the scent mixture formula. For example, the scent mixture is generated shortly after the scent mixture formula is received. In another embodiment, generation of the scent mixture specified by the received scent mixture formula is triggered by the user of the receiving hand-held device. That is, once a scent mixture formula is received at the hand-held device, the corresponding scent mixture is only generated at the discretion of the user. In still another embodiment, generation of the scent mixture specified by the received scent mixture formula is triggered automatically at some designated time or upon some designated action. For example, the scent mixture formula may specify that the scent mixture be generated at a particular time and date or that the scent mixture formula be generated upon dialing of a specific telephone number or upon accessing a particular web address.

Figure 5:
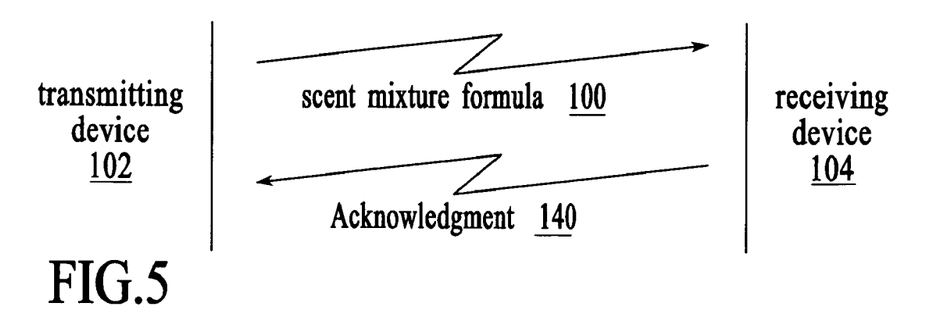
FIG. 5 illustrates a scent transmission protocol function in which a scent mixture formula is transmitted from a first hand-held device and an acknowledgement is generated by a second hand-held device in response to receiving the scent mixture formula.

The transmission of a scent mixture formula to a hand-held device may be accomplished according to a scent transmission protocol. A scent transmission protocol can perform different functions and some exemplary scent transmission protocol functions are described with reference to FIGS. 5-8. FIG. 5 illustrates a scent transmission protocol in which a scent mixture formula 100 is transmitted from a first hand-held device 102, referred to as the "transmitting device," and an acknowledgement 140 is generated by a second hand-held device 104, referred to as the "receiving device," in response to receiving the scent mixture formula. The acknowledgement may include, for example, an acknowledgement that the scent mixture formula was received, an indication as to the availability of the base scents that are included in the scent mixture formula, an indication of the amount of base scent material available before and/or after dispense, an indication that the scent mixture was actually dispensed, or any combination thereof.

Figure 6:
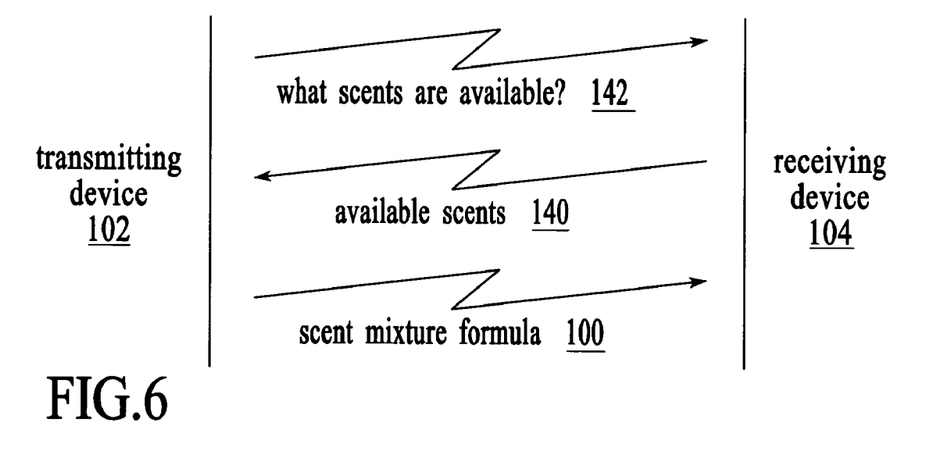
FIG. 6 illustrates a scent transmission protocol function in which the transmitting device queries the receiving device before transmitting a scent mixture formula.

FIG. 6 illustrates a scent transmission protocol function in which the transmitting device 102 queries the receiving device 104 before transmitting a scent mixture formula. In a first communication 142, the transmitting device queries the receiving device to see what base scents the receiving device has available. In a second communication 140, the receiving device indicates to the transmitting device which base scents it has available, an indication of the amount of base scent material available before and/or after dispense, or any combination thereof. The transmitting device evaluates the available base scents and in a third communication, transmits a scent mixture formula 100 to the receiving device. This scent transmission protocol function allows the transmitting device to learn what base scents the receiving device has before sending the scent mixture formula. If the receiving device is not capable of generating the desired scent mixture, the scent mixture formula may not be transmitted or a different scent mixture formula can be considered for transmission. Using this protocol, the scent mixture formula can be customized to the capability of the receiving device.

Figure 7:
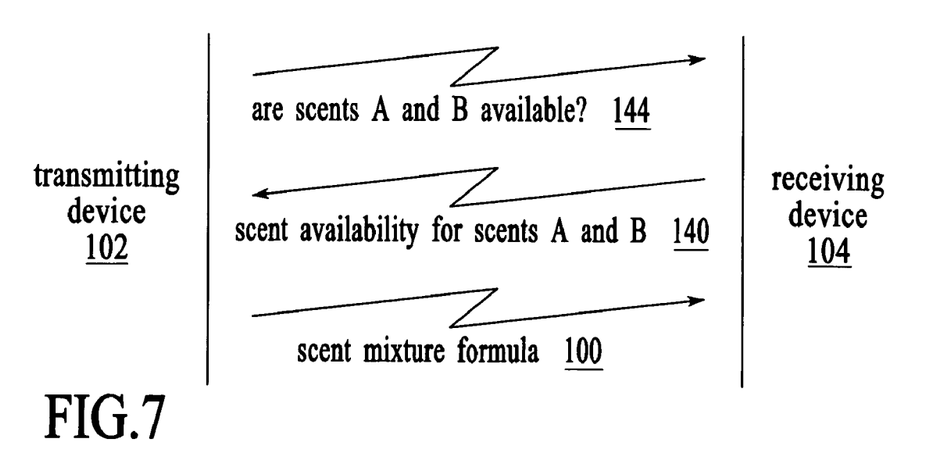
FIG. 7 illustrates another scent transmission protocol function in which the transmitting device queries the receiving device before transmitting a scent mixture formula.

FIG. 7 illustrates another scent transmission protocol function in which the transmitting device 102 queries the receiving device 104 before transmitting a scent mixture formula. In a first communication 144, the transmitting device queries the receiving device to see if the receiving device has available all of the base scents that are specified by a particular scent mixture formula. In a second communication 140, the receiving device indicates whether or not the specified base scents are available, an indication of the amount of base scent material available before and/or after dispense, or any combination thereof. The transmitting device checks the availability of the base scents before transmitting the scent mixture formula. In a third communication, the transmitting device transmits a scent mixture formula 100 to the receiving device. This protocol allows the transmitting device to know in advance whether or not the receiving device is capable of generating the desired scent mixture. If the receiving device is not capable of generating the desired scent mixture, the scent mixture formula may not be transmitted or a different scent mixture formula can be considered for transmission. Using this protocol, the scent mixture formula can be customized to the capability of the receiving device.

Figure 8:
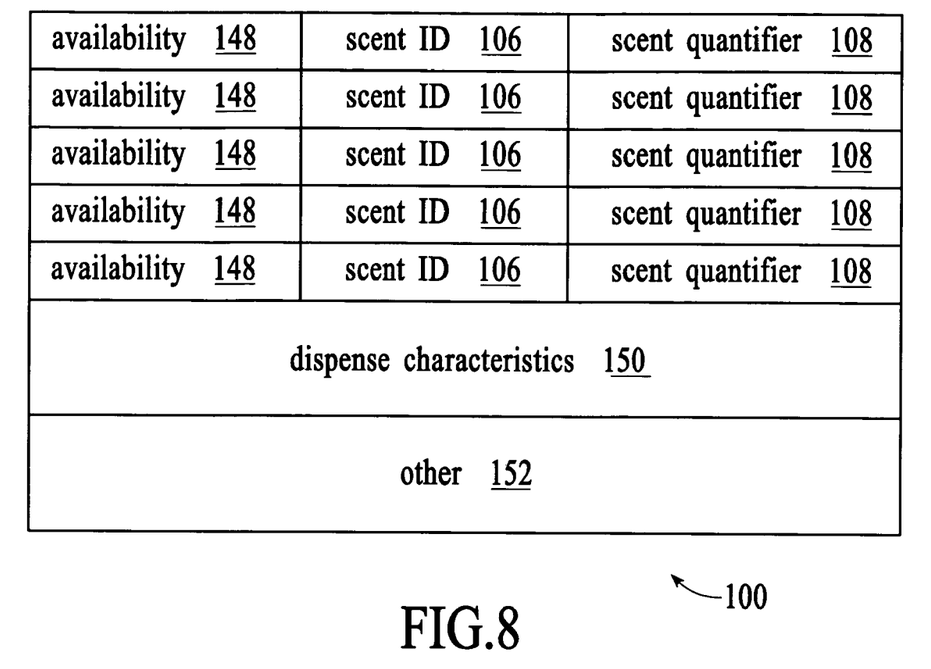
FIG. 8 depicts an example frame format for a scent mixture formula.

The scent mixture formula can include fields for carrying information in addition to scent ID and scent quantifier pairs. FIG. 8 depicts an exemplary frame format for a scent mixture formula that includes an availability field 148, a scent ID field 106, and a scent quantifier field 108 for each scent in a scent mixture formula. In the embodiment of FIG. 8, the availability field is used in an acknowledge message to indicate whether the related base scent is available for use in generating the corresponding scent mixture.

The frame format of FIG. 8 also includes a dispense characteristic field 150 that is used to convey any dispense characteristics that are associated with the generation of the scent mixture. Dispense characteristics conveyed through this field may include the time of dispense, the duration of dispense, the quantity of dispense, whether or not the dispensing is to be repeated, the interval of dispensing, etc. Although some dispense characteristics are identified, other characteristics related to dispensing a scent mixture can be specified in this field. The frame format may also include a field 152 for other information related to the scent mixture formula transmission.

Figure 9:
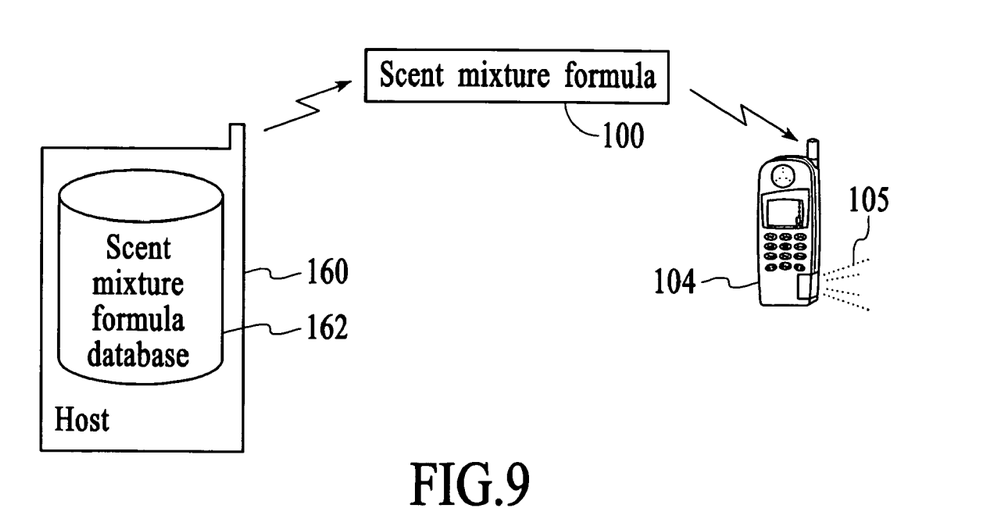
FIG. 9 illustrates a device that hosts a database of scent mixture formulas and a hand-held device that obtains a scent mixture formula from the scent mixture formula database.

As the number of different base scents stored in a hand-held device increases, the number of possible scent mixtures that can be created increases. In an embodiment, a large number of scent mixture formulas are stored in a centralized scent mixture formula database that can be accessed by a hand-held device. FIG. 9 illustrates a host device 160 that hosts a scent mixture formula database 162 and a hand-held device 104 that obtains a scent mixture formula 100 from the scent mixture formula database. In an exemplary operation, the hand-held device accesses the scent mixture formula database and selects a desired scent mixture formula. At the scent mixture formula database, the scent mixture formulas can be catalogued for easy browsing. The desired scent mixture formula is then downloaded from the scent mixture formula database to the hand-held device. Once downloaded, the scent mixture formula can be used by the hand-held device to generate the corresponding scent mixture. In an embodiment, the scent mixture formulas are available for purchase from the scent mixture formula database on a per-use or subscription basis. For example, a single scent mixture formula can be purchased for a one-time download fee or unlimited access to multiple scent mixture formulas can be obtained for a subscription fee. In the embodiment of FIG. 9, the host of the scent mixture formula database includes a wireless interface that enables the scent mixture formula database to be accessed from a wireless hand-held device and scent mixture formulas to be transmitted to wireless hand-held devices. In an alternative embodiment, the wireless interface may be separate from the host device.

In one embodiment, the user of a hand-held device is notified when a scent mixture formula is received. In another embodiment, scent mixture formulas are received without notification to the user of the receiving hand-held device. Scent mixture formulas received at a hand-held device without notification to the user may include a dispense characteristic that causes the generation of the scent mixture to be a surprise to the user of the receiving hand-held device.

In an embodiment, the hand-held device 120 is configured to maintain indications of the remaining quantities of the different base scents in the scent dispense system 130. The indications may be, for example, binary scent-specific indications that the base scents remain or are empty or a more detailed accounting of the remaining quantities of base scents. The remaining quantities of base scents can be periodically updated by the scent dispense system. In an embodiment, remaining scent quantity information is included in an acknowledgement message that is provided to a transmitting device. The transmitting device can use the remaining quantity information to determine if it is possible for the receiving device to generate a particular scent mixture before sending the corresponding scent mixture formula.

Figure 10:
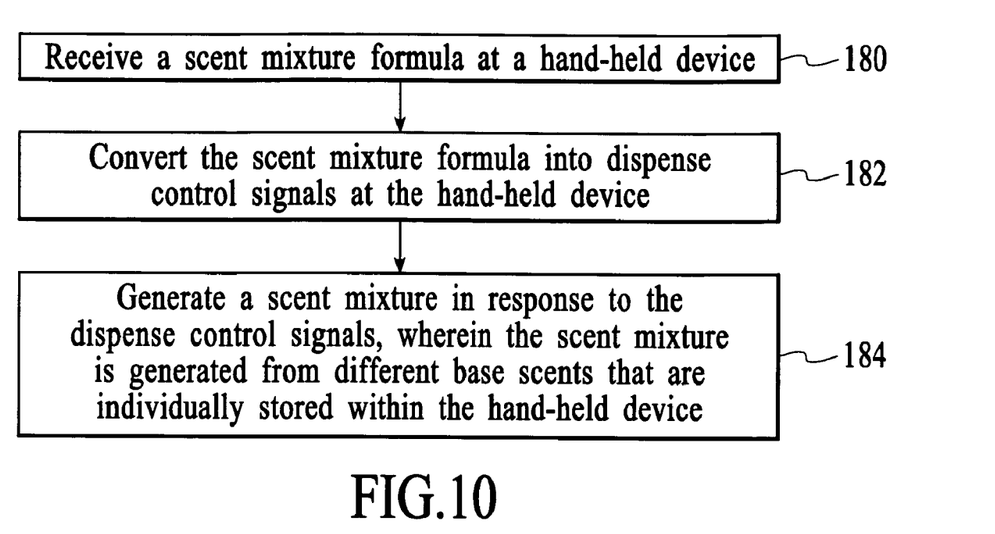
FIG. 10 is a process flow diagram of a method for producing a scent at a hand-held device.

FIG. 10 is a process flow diagram of a method for producing a scent at a hand-held device. At block 180, a scent mixture formula is received at a hand-held device. At block 182, the scent mixture formula is converted into dispense control signals at the hand-held device. At block 184, a scent mixture is generated in response to the dispense control signals, wherein the scent mixture is generated from different base scents that are individually stored within the hand-held device.

Figure 11:
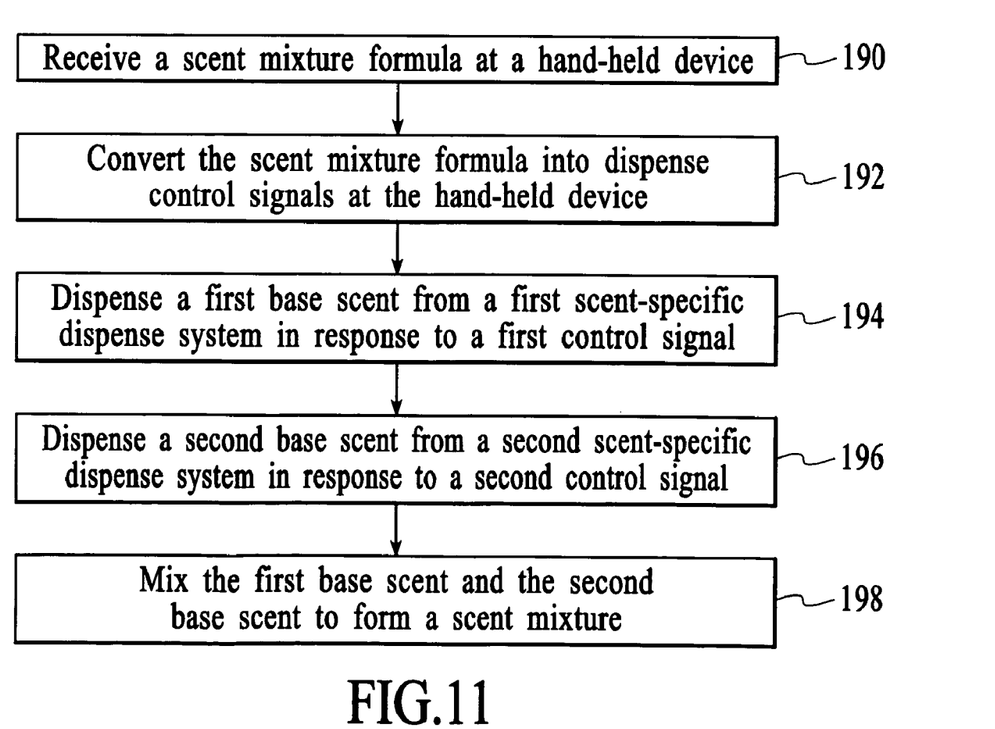
FIG. 11 is a process flow diagram of another method for producing a scent at a hand-held device.

FIG. 11 is a process flow diagram of another method for producing a scent at a hand-held device. At block 190, a scent mixture formula is received at a hand-held device. At block 192, the scent mixture formula is converted into dispense control signals at the hand-held device. At block 194, a first base scent is dispensed from a first scent-specific dispense system in response to a first control signal. At block 196, a second base scent is dispensed from a second scent-specific dispense system in response to a second control signal. At block 198, the first base scent and the second base scent are mixed to form a scent mixture.

Although specific embodiments of the invention have been described and illustrated, the invention is not to be limited to the specific forms or arrangements of parts so described and illustrated. The scope of the invention is to be defined by the claims appended hereto and their equivalents.

What is claimed is:

1. A method for producing a scent at a hand-held device, the method comprising:
   receiving a scent mixture formula at a hand-held device;
   converting the scent mixture formula into dispense control signals at the hand-held device;
   generating a scent mixture in response to the dispense control signals, wherein the scent mixture is generated from different base scents that are individually stored within the hand-held device; and
   sending a response from the hand-held device indicating one of whether the base scents indicated in the scent mixture formula are available at the hand-held device, the amount of base scents available before dispensing, and the amount of base scents available after dispensing.

2. The method of claim 1 wherein the scent mixture formula comprises scent identifiers and scent quantifiers.

3. The method of claim 2 wherein the scent quantifiers indicate proportions of the base scents.

4. The method of claim 1 wherein the scent mixture formula comprises multiple scent identifier and scent quantifier pairs.

5. The method of claim 1 wherein generating the scent mixture comprises dispensing the different base scents.

6. The method of claim 5 wherein dispensing the different base scents comprises individually activating different scent-specific dispense systems.

7. The method of claim 1 wherein the scent mixture formula comprises a dispense characteristic.

8. The method of claim 1 additionally comprising receiving the scent mixture formula from a scent mixture formula database.

9. The method of claim 8 further comprising paying a fee for receiving the scent mixture formula from the scent mixture formula database.

10. The method of claim 1 further comprising receiving the scent mixture formula wirelessly.

11. The method of claim 1 wherein the scent mixture formula is wirelessly received from another hand-held device.

12. A method for producing a scent at a hand-held device, the method comprising:
    receiving a scent mixture formula at a hand-held device;
    converting the scent mixture formula into dispense control signals at the hand-held device;
    dispensing a first base scent from a first scent-specific dispense system in response to a first control signal;
    dispensing a second base scent from a second scent-specific dispense system in response to a second control signal;
    mixing the first base scent and the second base scent to form a scent mixture; and
    sending a response from the hand-held device indicating one of whether the base scents indicated in the scent mixture formula are available at the hand-held device, the amount of base scents available before dispensing, and the amount of base scents available after dispensing.

13. The method of claim 12 wherein the scent mixture formula comprises scent identifiers and scent quantifiers.

14. The method of claim 13 wherein the scent quantifiers indicate scent proportions.

15. The method of claim 12 wherein the scent mixture formula comprises multiple scent identifier and scent quantifier pairs and a dispense characteristic.

16. The method of claim 12 wherein generating the scent mixture comprises dispensing the first and second base scents by individually activating different scent-specific dispense systems.

17. A hand-held device comprising:
    an input/output (I/O) interface configured to receive a scent mixture formula;
    scent control logic configured to convert the scent mixture formula into dispense control signals;
    a scent dispense system comprising first and second scent-specific dispense systems that store different base scents, wherein the scent dispense system is configured to generate a scent mixture upon activation of the first and second scent-specific dispense systems in response to the dispense control signals from the scent control logic; and
    a scent transmission protocol module configured to generate a response from the hand-held device indicating one of whether scented materials indicated in the scent mixture formula are available at the hand-held device, the amount of base scents available before dispensing, and the amount of base scents available after dispensing.

18. The hand-held device of claim 17 wherein the scent mixture formula comprises multiple scent identifier and scent quantifier pairs.

19. The hand-held device of claim 17 further comprising the scent transmission protocol module configured to support encoding and decoding of scent mixture formulas.

* * * * *